(12) United States Patent
Ziolo

(10) Patent No.: US 9,345,521 B2
(45) Date of Patent: May 24, 2016

(54) ADJUSTABLE ROD CONNECTOR

(71) Applicant: BLACKSTONE MEDICAL, INC., Lewisville, TX (US)

(72) Inventor: Tara Ziolo, Hewitt, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 117 days.

(21) Appl. No.: 13/839,106

(22) Filed: Mar. 15, 2013

(65) Prior Publication Data

US 2014/0277160 A1  Sep. 18, 2014

(51) Int. Cl.
*A61B 17/70* (2006.01)

(52) U.S. Cl.
CPC ................. *A61B 17/7049* (2013.01)

(58) Field of Classification Search
CPC .......... A61B 17/7032; A61B 17/7034; A61B 17/7049; A61B 17/705
USPC ................... 606/250–253, 260, 278
See application file for complete search history.

(56) References Cited

U.S. PATENT DOCUMENTS

| | | | |
|---|---|---|---|
| 2005/0228378 A1* | 10/2005 | Kalfas | A61B 17/705 606/252 |
| 2006/0079892 A1* | 4/2006 | Roychowdhury et al. | 606/61 |
| 2010/0280552 A1* | 11/2010 | Lee | A61B 17/705 606/250 |
| 2012/0029571 A1 | 2/2012 | Schwab et al. | |

FOREIGN PATENT DOCUMENTS

EP            1443864 B1    10/2007

* cited by examiner

*Primary Examiner* — Ellen C Hammond
*Assistant Examiner* — Christina Negrellirodriguez
(74) *Attorney, Agent, or Firm* — Baker & McKenzie LLP

(57) ABSTRACT

Example embodiments relate to systems and apparatuses for securing surgically implantable implantation rods, comprising a first body having a recessed portion formed by a first surface of the first body, a second body having a recessed portion formed by a first surface of the second body, and a connecting member having an elongated body defining a common longitudinal axis for the first body and the second body, the connecting member receivable in the recessed portion of the first body and the recessed portion of the second body. The connecting member is operable to cooperate with the first body to restrict movement of the first body relative to the second body about the common longitudinal axis when engaged in a substantially locked position, and the first body is moveable relative to the second body when disengaged from the substantially locked position.

34 Claims, 11 Drawing Sheets

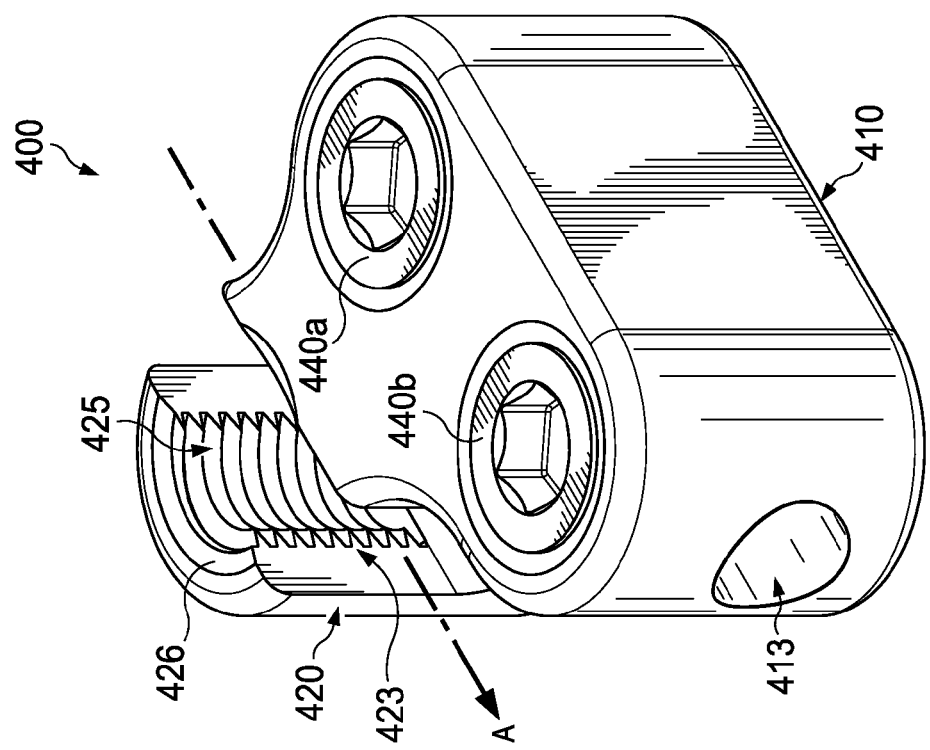

ADJUSTABLE ROD CONNECTOR

TECHNICAL FIELD

The present disclosure relates generally to systems and apparatuses for use with surgically implantable elements. More specifically, the present disclosure relates generally to implantation rod connector systems for use in securing surgically implantable implantation rods.

BACKGROUND

Due to various genetic and/or developmental occurrences, including diseases, developmental irregularities, trauma, stress, and the like, one or more bones may require surgical intervention. To protect and/or aid in the recovery of one or more surgically repaired bones, such as a section of the spinal column, there are often situations wherein it is desirable to collectively restrict movement of one or more bones.

Today, immobilization of one or more bones in the human body may be achievable using one of a variety of surgically implantable support systems and methods. In general, one or more surgically-implantable rods are fixedly attached by threading one or more anchor screws to a bone, such as a pedicle of one or more vertebrae of the spinal column. Each anchor screw is in turn fixedly coupled to the implantation rod at proximate locations along its shaft.

In certain situations, it may be desirable to increase the support and/or torsional rigidity of the surgically-implantable implantation rod system. These situations may require not only support on the bone that is attached to an implantation rod, but also torsional rigidity and/or support collectively between implantation rods. In certain situations, such implantation rods may not be in an ideal positional relationship with respect to each other. For example, the implantation rods may have already been implanted in such a way that the implantation rods are not parallel with each other. As another example, there may be situations wherein a suitable implantation is one where the implantation rods are not in parallel with each other. In such situations, problems arise since conventional connectors between implantation rods generally require the implantation rods to be substantially parallel with each other in order to achieve a proper connection between the implantation rods. Conventional solutions to such problems generally require, among other things, one or more implantation rods to be precisely adjusted, such as by bending, so as to create a substantially parallel region for the connectors to be attached. It is recognized herein that such precise adjustments not only require customized adjustments, which can be very expensive and time-consuming, but may also affect the structural integrity of the implantation rod(s).

SUMMARY

Present example embodiments relate generally to systems and apparatuses for use with surgically implantable elements. More specifically, the present disclosure relates generally to implantation rod connector systems for use in securing surgically implantable implantation rods.

In an exemplary embodiment, an apparatus is provided for use in securing one or more surgically implantable implantation rods, the apparatus comprising a first body having a first recessed portion of the first body formed by a first surface of the first body. The apparatus may also comprise a second body having a first recessed portion of the second body formed by a first surface of the second body. The apparatus may also comprise a connecting member having an elongated body defining a common longitudinal axis for the first body and the second body, the connecting member receivable in the first recessed portion of the first body and the first recessed portion of the second body. In example embodiments, the connecting member is operable to cooperate with the first body to restrict movement of the first body relative to the second body about the common longitudinal axis when engaged in a substantially locked position, and the first body is moveable relative to the second body when disengaged from the substantially locked position.

In another exemplary embodiment, an apparatus is provided for use in securing one or more surgically implantable implantation rods, the apparatus comprising a connecting member comprising an elongated body defining a common longitudinal axis. The apparatus may also comprise a first body comprising a first recessed portion of the first body operable to receive the connecting member and a second recessed portion of the first body operable to receive a first implantation rod portion, the first and second recessed portions of the first body formed by a first and a second surface of the first body, respectively. The apparatus may also comprise a second body comprising a first recessed portion of the second body operable to receive the connecting member and a second recessed portion of the second body operable to receive a second implantation rod portion, the first and second recessed portions of the second body formed by a first and a second surface of the second body, respectively. The apparatus may also comprise a first restriction portion comprising one or more of a recessed portion and a protruding portion of the first restriction portion formed by a surface of the first restriction portion. The apparatus may also comprise a second restriction portion comprising one or more of a recessed portion and a protruding portion of the second restriction portion formed by a surface of the second restriction portion. In example embodiments, movement of the first body relative to the second body about the common longitudinal axis is restrictable when the first restriction portion and the second restriction portion are engaged in an interlocking manner and the connecting member is secured in the first body and the second body.

In another exemplary embodiment, an apparatus is provided for use in securing one or more surgically implantable implantation rods, the apparatus comprising a connecting member comprising a first end formed by a first end outer surface, a second end formed by a second end outer surface, and an elongated body in communication with the first end and the second end, the elongated body operable to define a common longitudinal axis. The apparatus may also comprise a first body. The first body may comprise a first recessed portion of the first body operable to receive at least the first end of the connecting member, the first recessed portion of the first body formed by a first surface of the first body. The first body may also comprise a second recessed portion of the first body operable to receive a first implantation rod portion, the second recessed portion of the first body formed by a second surface of the first body. The first body may also comprise a first restriction portion comprising one or more of a recessed portion and a protruding portion of the first restriction portion formed by a third surface of the first body. The apparatus may also comprise a second body. The second body may comprise a first recessed portion of the second body operable to receive at least the second end of the connecting member, the first recessed portion of the second body formed by a first surface of the second body. The second body may also comprise a second recessed portion of the second body operable to receive a second implantation rod portion, the second recessed portions of the second body formed by a second surface of the second body. The second body may also comprise a second restriction portion comprising one or more of a recessed portion and a protruding portion of the second restriction portion formed by a third surface of the second body. In example embodiments, movement of the first body relative to the second body about the common longitudinal axis is restrictable when the one or more of the recessed portion and the protruding portion of the first restriction portion and the one or more of the recessed portion and the protruding portion of the second restriction portion are mated and persistently urged together by the connecting member.

BRIEF DESCRIPTION OF THE DRAWINGS

For a more complete understanding of the present disclosure and its advantages, reference is now made to the following description taken in conjunction with the accompanying drawings, in which like reference numbers indicate like features, and:

FIG. 4 is an example illustration of a perspective view of another example embodiment of an implantation rod connector system;

Although similar reference numbers may be used to refer to similar elements for convenience, it can be appreciated that each of the various example embodiments may be considered to be distinct variations.

DETAILED DESCRIPTION

Figure 1A:
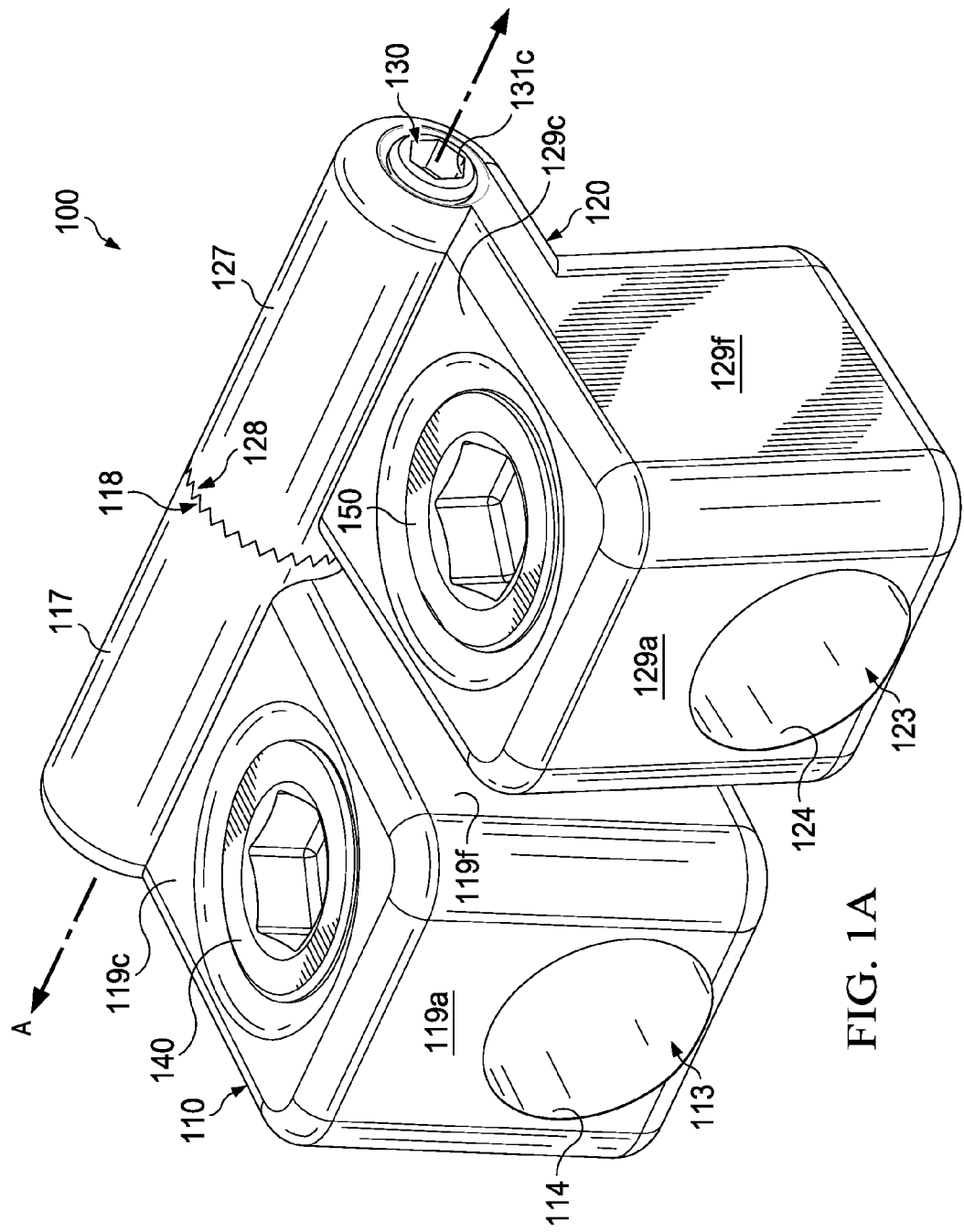
FIG. 1A is an example illustration of a perspective view of an example embodiment of an implantation rod connector system.

Present example embodiments will now be described hereinafter with reference to the accompanying drawings, which form a part hereof, and which illustrate example embodiments which may be practiced. As used in the disclosures and the appended claims, the terms "example embodiment" and "exemplary embodiment" are interchangeable and do not necessarily refer to a single embodiment, although it may, and various example embodiments may be readily combined and interchanged, without departing from the scope or spirit of example embodiments. Furthermore, the terminology as used herein is for the purpose of describing example embodiments only and is not intended to be limitations. In this respect, as used herein, the term "in" may include "in" and "on", and the terms "a", "an" and "the" may include singular and plural references. Furthermore, as used herein, the term "by" may also mean "from", depending on the context. Furthermore, as used herein, the term "if" may also mean "when" or "upon", depending on the context. Furthermore, as used herein, the words "and/or" may refer to and encompass any and all possible combinations of one or more of the associated listed items.

In general, non-ideal situations frequently occur in patients requiring increased support and/or torsional rigidity within and/or between bones supported by surgically implantable implantation rods. Because conventional connector systems are best suited for attaching in substantially ideal situations, surgeons are often faced with having to either perform precise adjustments of implantation rods, such as bending of one or more portions of one or more implantation rods, and/or perform complicated surgical re-adjustments of already-implanted implantation rod systems, so as to accommodate the connecting of conventional connector systems. Surgical re-adjustments may include removing of hooks, anchor screws, coupling components, and/or implantation rods, and re-threading the anchor screws and/or re-installing the components in a different location, position, and/or orientation, so as to enable the implantation rods to be substantially parallel and/or having sufficient separation distance between the implantation rods.

In practice, surgeons are often faced with practical problems and difficulties in implanting surgically implantable implantation rods in patients to be substantially parallel and/or having sufficient separation distance due to, among other things, the anatomically varying sizes, shapes, and/or orientations of bones and relative positions thereof, and/or the varying degrees and/or nature of surgical repairs required and/or rendered to bones of each particular patient. In such situations, surgeons may have little or no choice other than to implant implantation rods in non-ideal positions relative to each other. This in turn makes it difficult to properly couple conventional connector systems to such implantation rods. Thereafter, surgeons may often be required to perform precise adjustments of the implantation rods and/or complicated surgical re-adjustments of the implanted rods and/or anchor screws to accommodate conventional connector systems. A tremendous amount of time, planning, effort, precision, and cost may be incurred since these solutions typically involve, among other things, performing the precise adjustments of the implantation rods and/or surgically removing one or more anchor screws, coupling components, and/or implantation rods, and surgically re-installing them in such a way as to properly accommodate a substantially ideal position of the implantation rods, as required by conventional connector systems.

In general, fixation of one or more implantation rods to one or more bones may be provided by one or more fastener elements, such as an anchor screw. Typically, one or more anchor screws will be fixedly installed to a bone, such as a pedicle of one or more vertebrae, and correspondingly fixedly coupled about proximate sections of the shaft of the implantation rod. In many situations, a connector apparatus may be required between two implantable or implanted implantation rods, particularly when enhanced support and/or torsional rigidity is required. Hereinafter, an "implanted implantation rod" will refer to an implantation rod that has already been fixedly coupled to one or more bones.

In considering the above problems, it is recognized herein that providing increased support and/or torsional rigidity between implantation rods that require implantation or have already been implanted in non-ideal positions can be achieved without the need to perform precise adjustments of the implantation rods, such as bending, and/or surgical re-adjustments, re-positioning, and/or re-orientating of surgically implantable elements, such as implantation rods, coupling components, and/or anchor screws.

Present example embodiments are directed to apparatuses operable to secure one or more surgically implantable implantation rods and comprise a first body having a first recessed portion of the first body formed by a first surface of the first body. The apparatus may also comprise a second body having a first recessed portion of the second body formed by a first surface of the second body. The apparatus may also comprise a connecting member having an elongated body defining a common longitudinal axis for the first body and the second body, the connecting member receivable in the first recessed portion of the first body and the first recessed portion of the second body. In example embodiments, the connecting member is operable to cooperate with the first body to restrict movement of the first body relative to the second body about the common longitudinal axis when engaged in a substantially locked position, and the first body is moveable relative to the second body when disengaged from the substantially locked position.

Figure 1B:
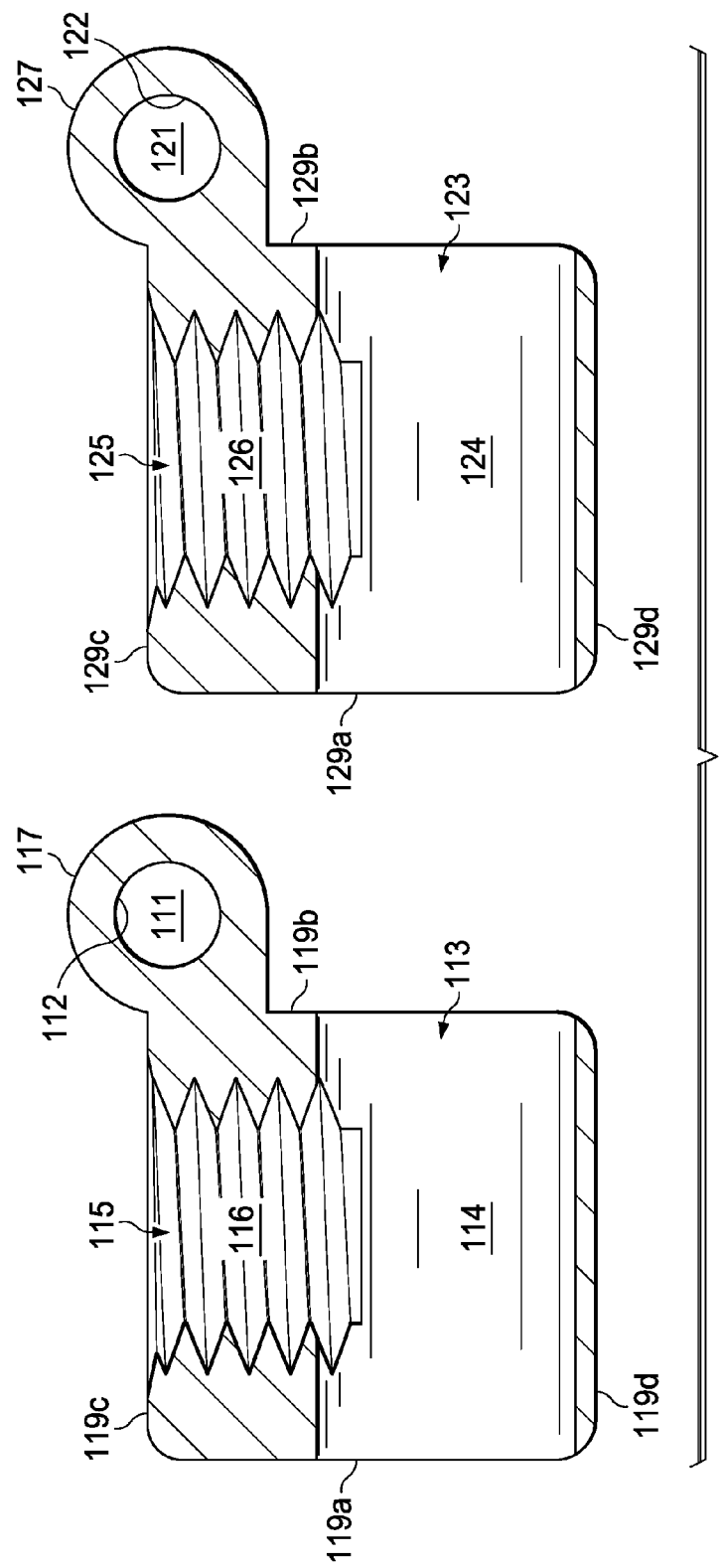
FIG. 1B is an example illustration of a cross-sectional side view of an example embodiment of an implantation rod connector system.
Figure 1C:
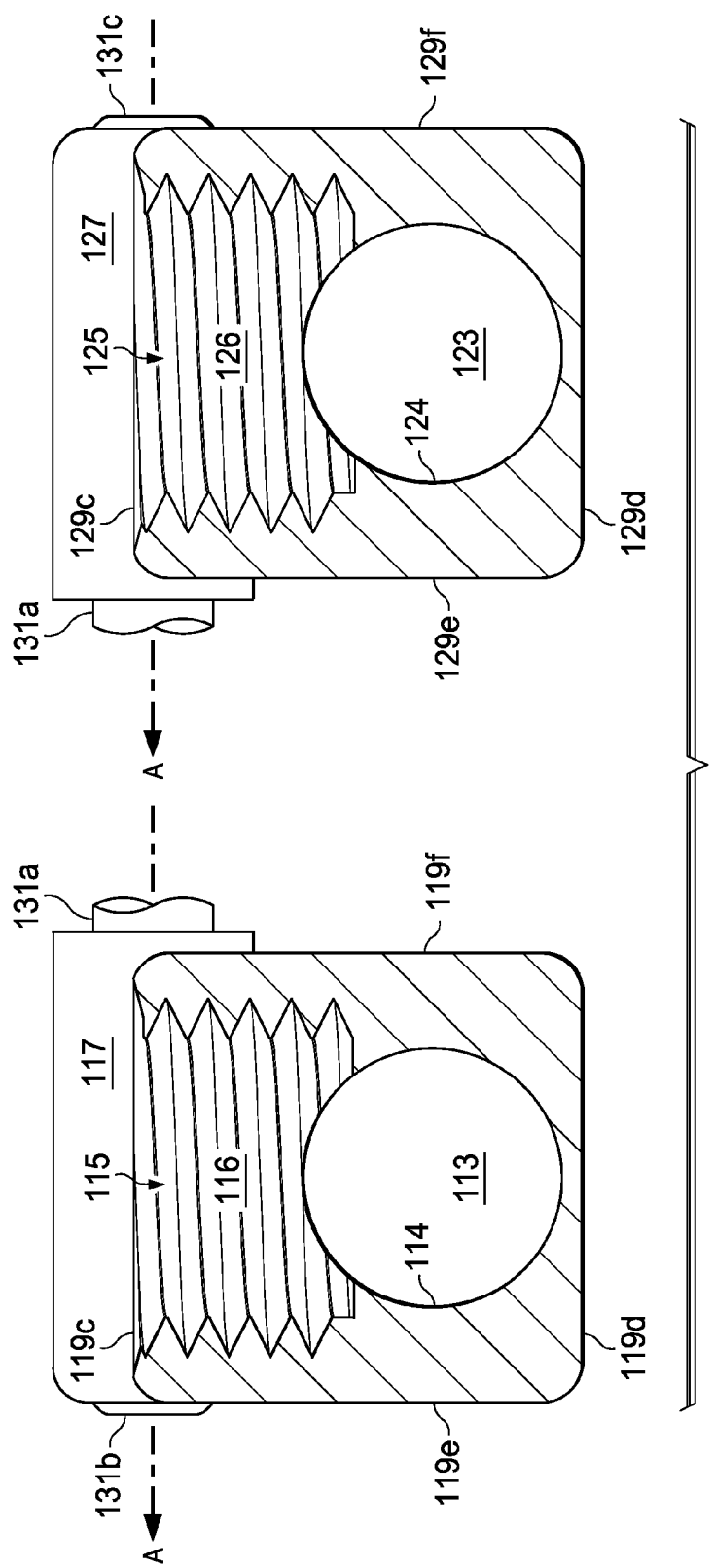
FIG. 1C is an example illustration of a cross-sectional front view of an example embodiment of an implantation rod connector system.

Reference is now made to an example embodiment of implantation rod connector system 100 illustrated in FIGS. 1A, 1B, and 1C comprising a connecting member 130, a first body 110, and a second body 120.

Connecting member 130 may comprise one or more parts and/or portions, including an elongated portion 131*a*, a first end 131*b*, and a second end 131*c*. The connecting member 130 is operable to be received in one or more recessed portions 111 and 121 of the first body 110 and the second body 120. In an example embodiment, the connecting member 130 may comprise an elongated body, such as one resembling or being a screw, having a head being the first end, such as a head having a variety of possible shapes, and an end being the second end, such as a threaded end. The connecting member 130 may also comprise an elongated member, a head being a first end, and a corresponding coupling element (not shown), such as a nut, being a detachable second end. The connecting member 130 may also comprise an elongated portion, such as one resembling or being a screw, with one or more restriction portions (to be further described) operable to secure with one or more mateable portions of the first body 110 and/or the second body 120. It is to be understood herein that the connecting member 130 may be of any elongated shape, size, parts, and portions, so long as the connecting member 130 is operable to be received in and secured about one or more recessed portions 111 and 121 of the first body 110 and the second body 120.

When the connecting member 130 is received in one or more recessed portions 111 of the first body 110 and one or more recessed portions 121 of the second body 120, the connecting member 130 is operable to define an imaginary common longitudinal axis A for the first body 110 and the second body 120. In operation, the connecting member 130 may cooperate with a portion 118 and/or 128 of the first body 110 and/or the second body 120 to fixably secure the position and restrict movement, including rotational and translational, of the first body 110 relative to the second body 120 about the common longitudinal axis A when the connecting member 130 is engaged in a substantially locked position. An example of a substantially locked position occurs when the elongated portion of the connecting member 130 is substantially provided in such a way that at least one or more of a first restriction portion (such as 118, 218, 318, 618, and 718) of the first body (such as 110, 210, 310, 610, and 710), a second restriction portion (such as 128, 228, 328, 628) of the second body (such as 120, 220, 320, 620, and 720), a restriction portion (such as 338 and 738) of the connecting member (such as 330 and 730), and/or a restriction portion (not shown) of an extension member (to be described later) is/are operable to securably restrict movement, including rotational and translational movement, of the first body relative to the second body about the common longitudinal axis A. For example, a substantially locked position may be achieved when one or more said restriction portions of the first body, the second body, the connecting member, and/or the extension member are mated and persistently urged together by the connecting member. In an example embodiment, the connecting member 130 may perform such persistent urging when coupled with one or more corresponding coupling portions, such as a threadable or latchable portion of the first body 110, a threadable or latchable portion of the second body 120, and/or a threadable or latchable coupling element such as a nut, or the like. It is to be understood herein that a restriction portion may be engaged in the substantially locked position when the connecting member is engaged in the substantially locked position.

When not in a substantially locked position, example embodiments enable the first body 110 and/or the second body 120 to be rotatable, as depicted by directional arrows A1 and A2 for the first body 110 and the second body 120, respectively, with respect to the common longitudinal axis A and/or with respect to one another about the common longitudinal axis A. It is recognized herein that such operability to move or rotate A1 and A2 one or more of the first body 110 and the second body 120 when not in a substantially locked position and before achieving said substantially locked position provides for, among other things, flexibility in adjustably adapting to non-ideal implantation rod situations. In example embodiments, the first body 110 and/or the second body 120 may advantageously provide for, among other things, further flexibility, adjustability, and adaptability to non-ideal implantation rod situations, as described below and herein.

The first body 110 may comprise one or more first recessed portions 111 of the first body 110 formed by one or more first surfaces 112 of the first body 110, one or more second recessed portions 113 of the first body 110 formed by one or more second surfaces 114 of the first body 110, and one or more first restriction portions 118 formed by one or more surfaces of the first restriction portion 118. The one or more first recessed portions 111 is/are operable to receive the connecting member 130 in one or more manners described above and herein. The first body 110 may further comprise one or more implantation rod securing assemblies comprising one or more first set screw recessed portions 115 formed by one or more first set screw recessed surfaces 116 and one or more first set screws 140. The one or more first set screw recessed portions 115 is/are operable to receive the one or more first set screws 140. When a first implantation rod portion (not shown) is received in the one or more second recessed portions 113 of the first body 110 and the one or more first set screws 140 is/are engaged in a substantially locked position, the one or more first set screws 140 is/are operable to secure the first implantation rod portion with respect to the first body 110.

The one or more first set screws 140 may be engageable in a substantially locked position when the one or more first set screws 140 is/are threaded into one or more corresponding threaded first set screw recessed surfaces 116 until an end surface of the one or more first set screws 140 comes in contact with a surface of the first implantation rod portion. It is to be understood herein that a first implantation rod securing assembly is engaged in the substantially locked position when its corresponding one or more first set screws are engaged in the substantially locked position. It is also to be understood herein that example embodiments may secure the first implantation rod portion with respect to the first body 110 in other ways, such as through use of one or more set cams, etc.

As illustrated, the first body 110 may further comprise a front side 119a, a rear or back side 119b, a top side 119c, a bottom side 119d, a left side 119e, and/or a right side 119f.

Although the example embodiment of FIGS. 1A, 1B, and 1C illustrates a coupling portion 117 comprising a first recessed portion 111 of the first body 110 and a first restriction portion 118, wherein the coupling portion 117 protrudes from the back side 119b and top side 119c of the first body 110, it is to be understood herein that the coupling portion 117 may protrude from one or more other sides, or may not protrude from the first body 110 at all in example embodiments. The coupling portion 117 may also comprise more than one first recessed portions 111 of the first body 110, such as the example embodiment illustrated in FIGS. 2A, 2B, and 2C, and/or more than one first restriction portions 118.

Each of the one or more first recessed portions 111 of the first body 110 are recessed portions formed by one or more first surfaces 112 of the first body 110. The one or more first recessed portions 111 is/are operable to receive at least a part of the connecting member 130, such as the first end of the connecting member 130.

In the example embodiment shown in FIGS. 1A, 1B, and 1C, the second recessed portion 113 of the first body 110 includes a recessed portion on the front side 119a and the rear side 119b. In such a configuration, the second recessed portion 113 of the first body is operable to receive a first implantation rod portion (not shown) by way of insertion of an end of an implantation rod into the recessed portion on the front side 119a or the rear side 119b of the first body 110. Hereinafter, a first body 110 comprising one or more second recessed portions 113 of the first body 110 formed by a recessed portion on the front side 119a and/or the rear side 119b will be referred to as a "front loading" first body 110. It is to be understood herein that the one or more second recessed portions 113 of the first body 110 may be formable by a recessed portion on one or more of the front side 119a, rear or back side 119b, top side 119c, bottom side 119d, left side 119e, and right side 119f in example embodiments. Alternative implantation rod loading configurations contemplated in example embodiments include "top loading", "bottom loading", "left side loading", "right side loading", and "diagonal loading", which enable an implantation rod to be received by a recessed portion formed on one or more of the front side 119a, back side 119b, top side 119c, bottom side 119d, left side 119e, right side 119f, and sections between or sharing two or more sides. In respect to the said loading configurations of the first body 110, it is to be understood herein that the one or more second recessed portions 113 of the first body 110 may be formable on any one or more sides of the first body 110 so as to receive insertion of an end of and/or a side portion of the shaft of an implantation rod.

The second body 120 may comprise one or more first recessed portions 121 of the second body 120 formed by one or more first surfaces 122 of the second body 120, one or more second recessed portions 123 of the second body 120 formed by one or more second surfaces 124 of the second body 120, and one or more second restriction portions 128 formed by one or more surfaces of the second restriction portion 128. The one or more first recessed portions 121 of the second body 120 is/are operable to receive the connecting member 130 in one or more manners described above and herein. The second body 120 may further comprise one or more implantation rod securing assemblies comprising one or more second set screw recessed portions 125 formed by one or more second set screw recessed surfaces 126 and one or more second set screws 150. In this regard, the one or more second set screw recessed portions 125 is/are operable to receive the one or more second set screws 150. When a second implantation rod portion (not shown) is received in the one or more second recessed portions 123 of the second body 120 and the one or more second set screws 150 is/are engaged in a substantially locked position, the one or more second set screws 150 is/are operable to secure the second implantation rod portion with respect to the second body 120. The one or more second set screws 150 may be engageable in a substantially locked position when the one or more second set screws 150 is/are threaded into one or more corresponding threaded second set screw recessed surfaces 126 until an end surface of the one or more second set screws 150 comes in contact with a surface of the second implantation rod portion. It is to be understood herein that a second implantation securing rod assembly is engaged in the substantially locked position when its corresponding one or more first set screws are engaged in the substantially locked position. It is also to be understood herein that example embodiments may secure the second implantation rod portion with respect to the second body 120 in other ways, such as through use of one or more set cams, etc.

As illustrated, the second body 120 may further comprise a front side 129a, a rear or back side 129b, a top side 129c, a bottom side 129d, a left side 129e, and/or a right side 129f.

Although the example embodiment of FIGS. 1A, 1B, and 1C illustrates a coupling portion 127 comprising a first recessed portion 121 of the second body and a second restriction portion 128, wherein the coupling portion 127 protrudes from the back side 129b and top side 129c of the second body 120, it is to be understood herein that the coupling portion 127 may protrude from one or more other sides, or may not protrude from the second body 120 at all in example embodiments. The coupling portion 127 may also comprise more than one first recessed portions 121 of the second body 120, such as the example embodiment illustrated in FIGS. 2A, 2B, and 2C, and/or more than one second restriction portions 128.

Each of the one or more first recessed portions 121 of the second body 120 are recessed portions formed by one or more first surfaces 122 of the second body 120. The one or more first recessed portions 121 of the second body 120 is/are operable to receive at least a part of the connecting member 130, such as the second end of the connecting member 130.

In the example embodiment shown in FIGS. 1A, 1B, and 1C, the second recessed portion 123 of the second body 120 includes a recessed portion on the front side 129a and the rear side 129b. In such a configuration, the second recessed portion 123 of the second body is operable to receive a second implantation rod portion (not shown) by way of insertion of an end of the implantation rod into the recessed portion on the front side 129a or the rear side 129b of the second body 120. In a similar manner as described above for the first body 110, a second body 120 comprising one or more second recessed portions 123 of the second body 120 formed by a recessed portion on the front side 129a and/or the rear side 129b will be referred to as a "front loading" second body 120. It is to be understood herein that the one or more second recessed portions 123 of the second body 120 may be formable by a recessed portion on one or more of the front side 129a, rear side 129b, top side 129c, bottom side 129d, left side 129e, and right side 129f in example embodiments. Alternative implantation rod loading configurations contemplated in example embodiments include "top loading", "bottom loading", "left side loading", "right side loading", and "diagonal loading", which enable an implantation rod to be received by a recessed portion formed on one or more of the front side 129a, back side 129b, top side 129c, bottom side 129d, left side 129e, right side 129f, and sections between or sharing two or more sides. In respect to the said loading configurations of the second body 120, it is to be understood herein that the one or more second recessed portions 123 of the second body 120 may be formable on any one or more sides of the second body 120 so as to receive an insertion of an end of and/or a side portion of the shaft of an implantation rod.

Figure 2A:
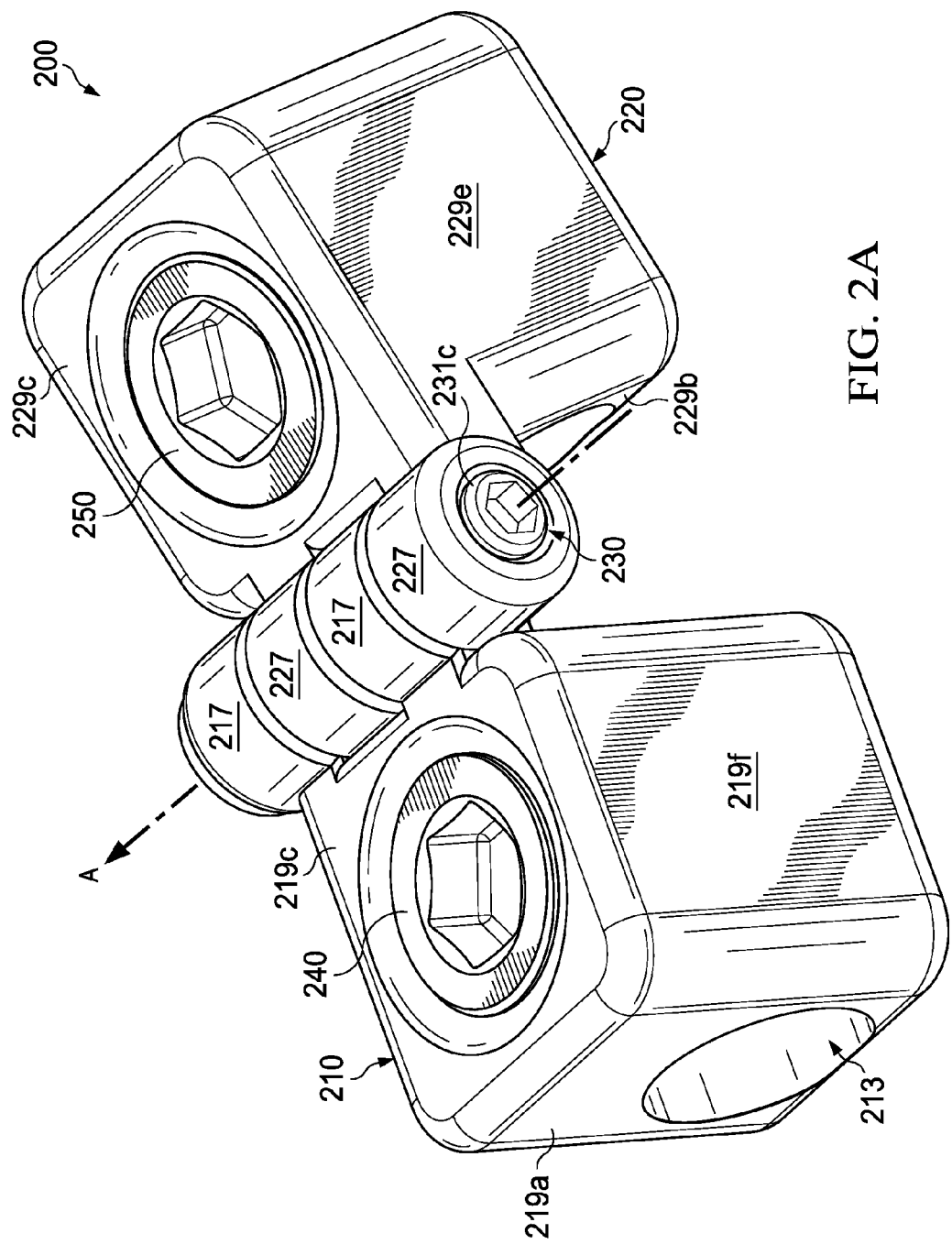
FIG. 2A is an example illustration of a perspective view of another example embodiment of an implantation rod connector system.
Figure 2B:
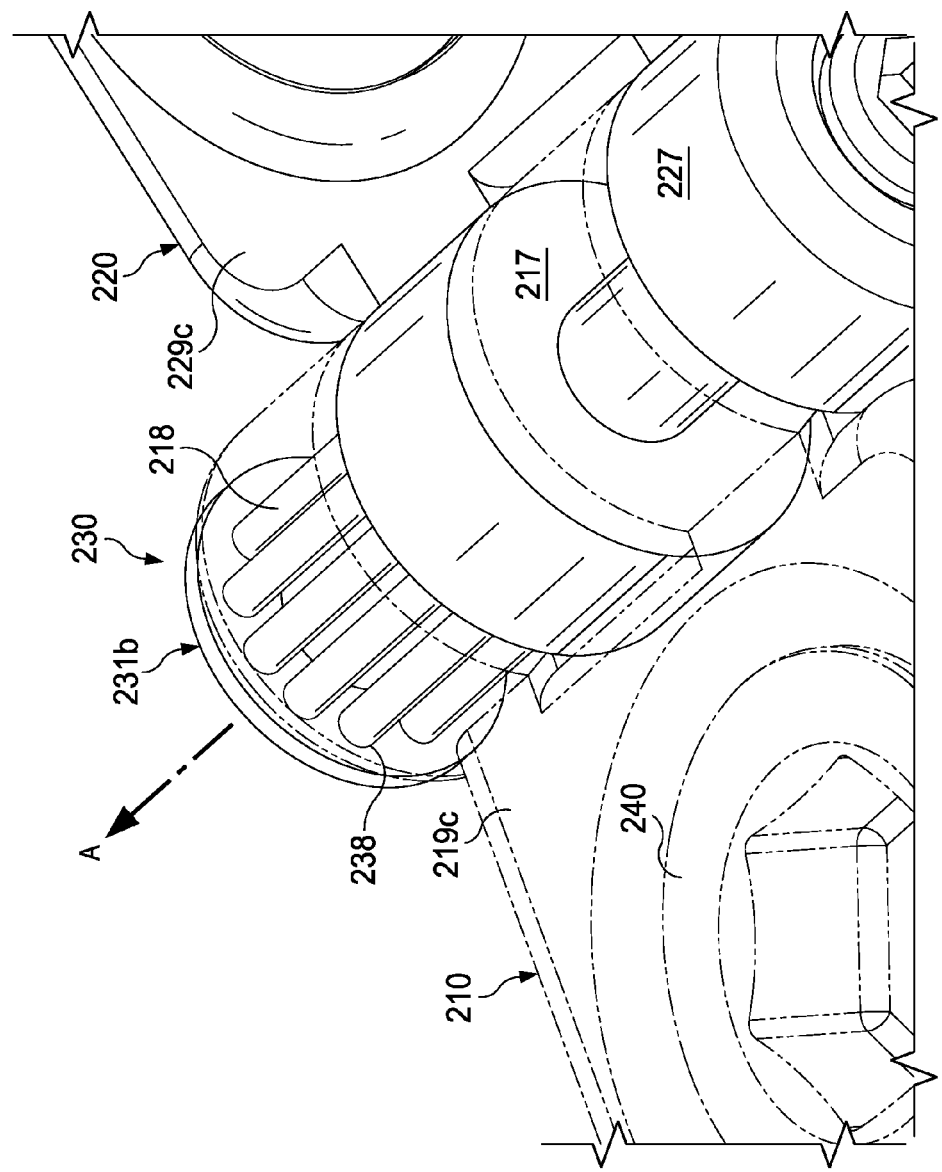
FIG. 2B is an example illustration of a perspective view of a portion of an example embodiment of an implantation rod connector system.
Figure 2C:
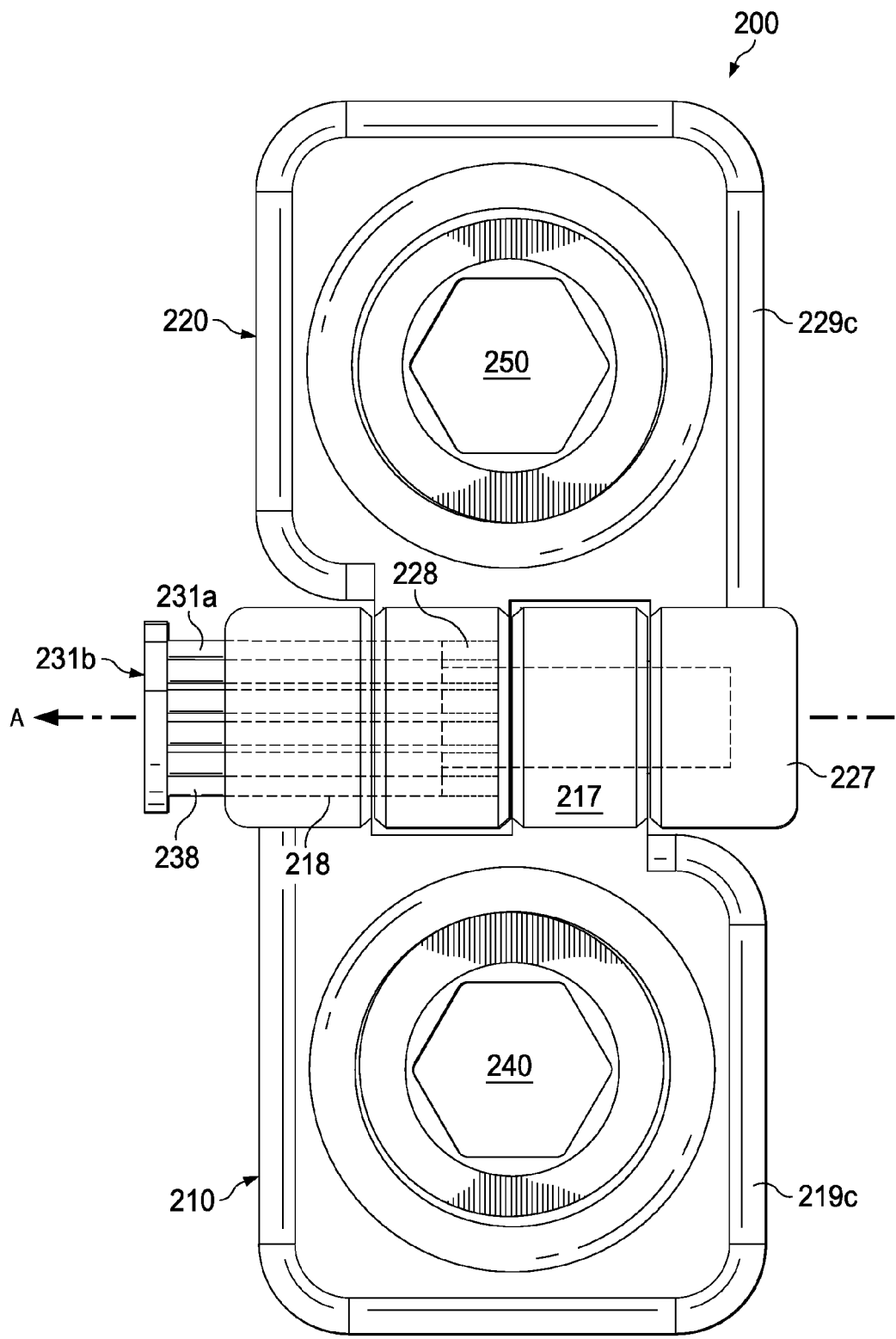
FIG. 2C is an example illustration of a top view of an example embodiment of an implantation rod connector system.
Figure 5:
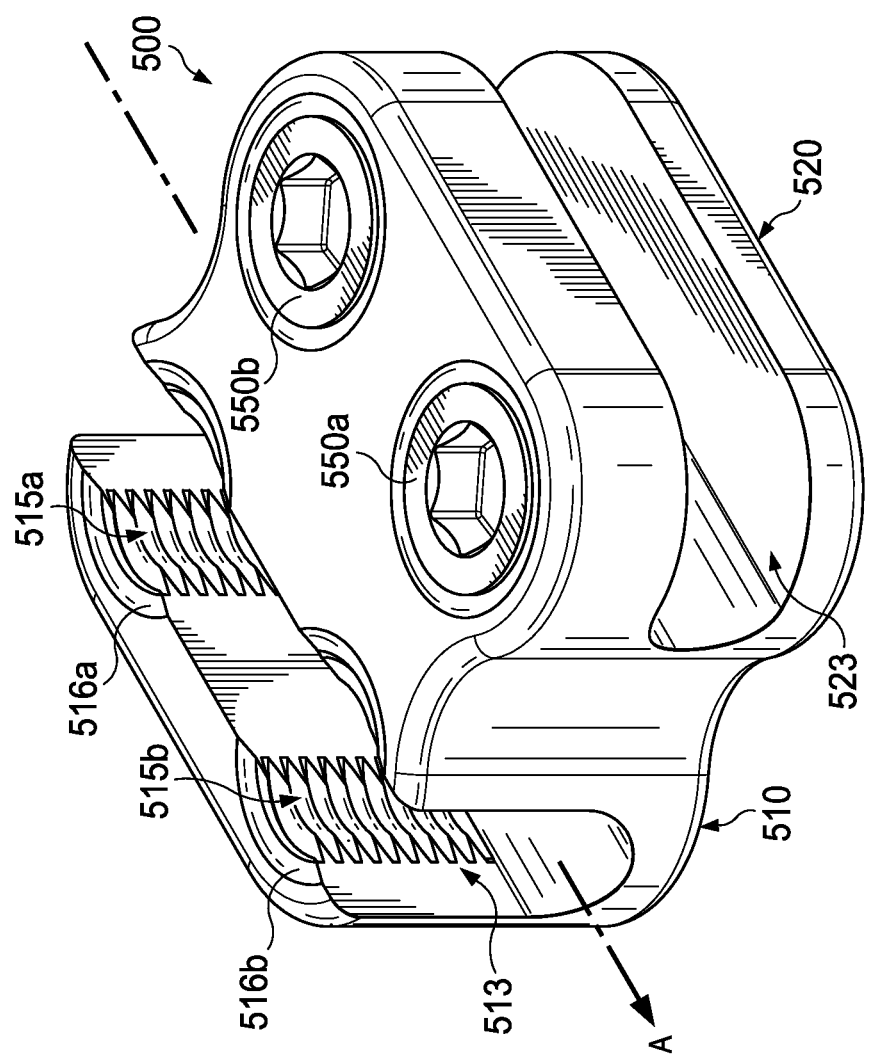
FIG. 5 is an example illustration of a perspective view of another example embodiment of an implantation rod connector system.
Figure 6:
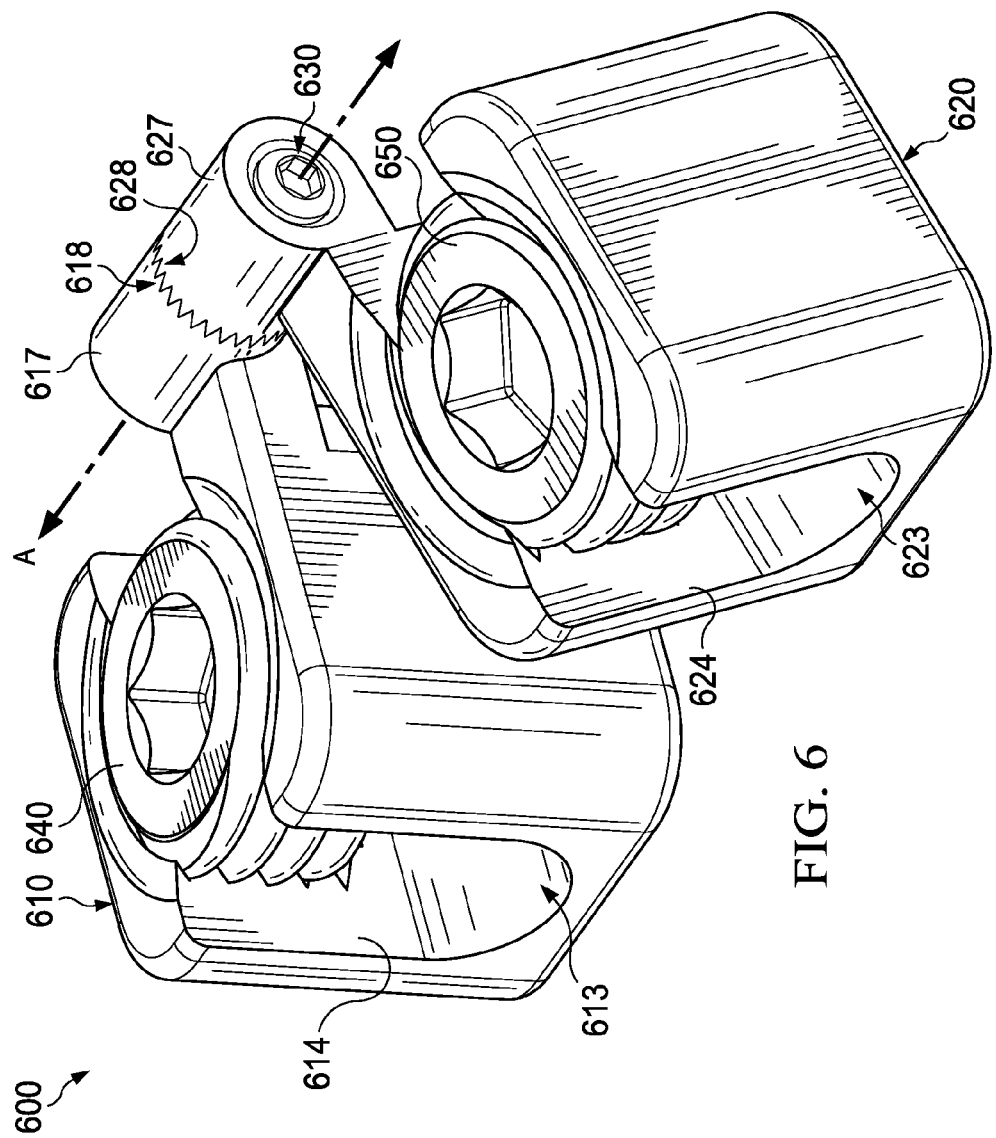
FIG. 6 is an example illustration of a perspective view of another example embodiment of an implantation rod connector system.
Figure 7:
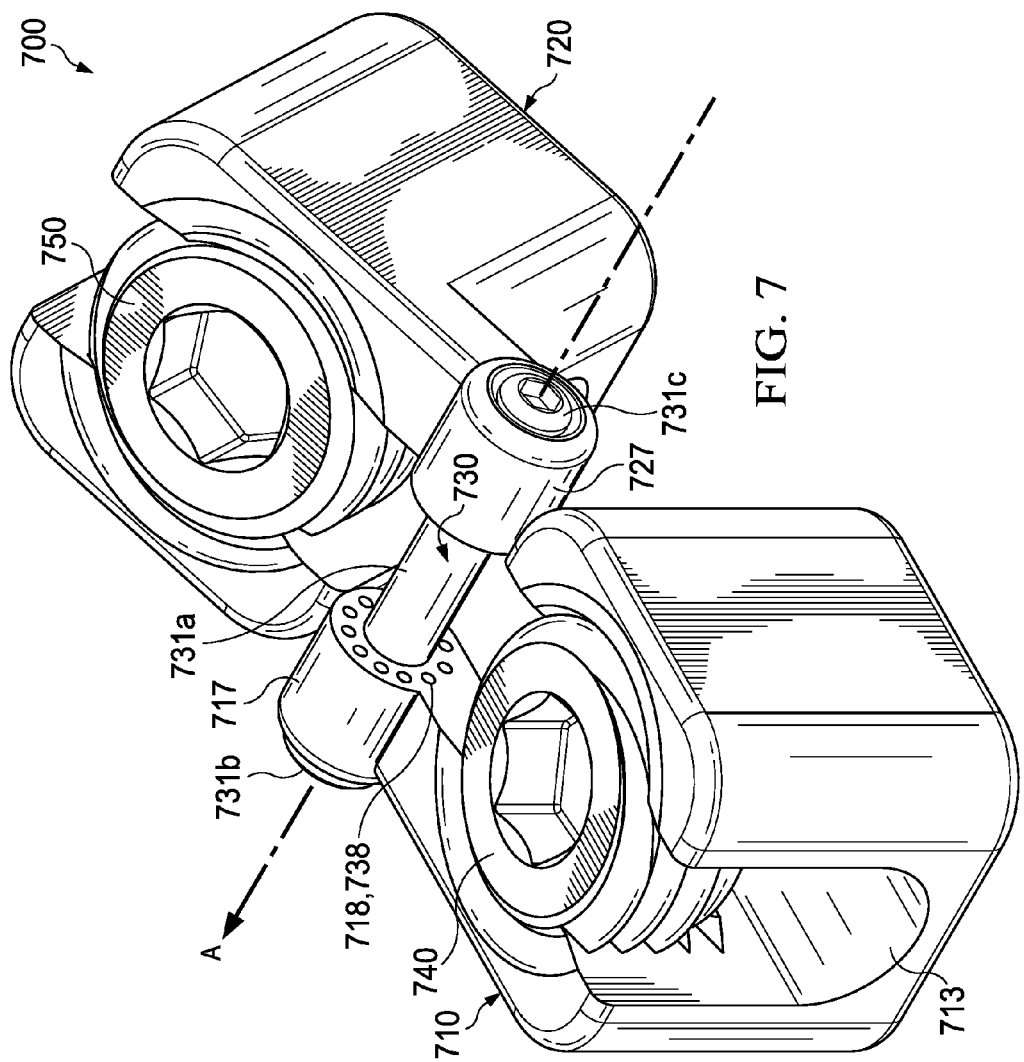
FIG. 7 is an example illustration of a perspective view of another example embodiment of an implantation rod connector system.

The first body 110 may be substantially the same as, and/or a substantial minor reflection of, the second body 120. An example embodiment of the former is illustrated in FIGS. 2A, 2B, and 2C, and an example embodiment of the latter is illustrated in FIGS. 1A, 1B, and 1C. The first body 110 and the second body 120 may also comprise one or more aspects that are oriented, positioned, and/or operated differently so as to accommodate specific situations, implantation rod arrangements, and/or implantation rod spacing. In other words, example embodiments of the implantation rod connector system 100 may be adaptively adjustable so as to enable securing of one or more implantation rods in a wide range of situations, orientations, positions, and spacing, including ideal and non-ideal situations. For example, the first body may comprise a body having a front loading configuration (or a "front loading body") and the second body may comprise a front loading body. Example embodiments of such configuration are illustrated in FIGS. 1A-C, 2A-C, and 3A. In another example embodiment, the first body may comprise a front loading body and the second body may comprise a body having a top loading configuration (or a "top loading body"). An example embodiment of such configuration is illustrated in FIG. 4. In another example embodiment, the first body may comprise a front loading body and the second body may comprise a body having a bottom loading configuration (or a "bottom loading body"). In another example embodiment, the first body may comprise a front loading body and the second body may comprise a body having a side loading configuration (or a "side loading body"), such as a right side loading body or a left side loading body. In another example embodiment, the first body may comprise a top loading body and the second body may comprise a top loading body. Example embodiments of such configuration are illustrated in FIGS. 6 and 7. As illustrated in the example embodiment of FIG. 6, system 600 comprises a first body 610, a second body 620, and connecting member 630. First and second bodies 610 and 620 comprise first recessed portions (shown receiving connecting member 630), second recessed portions 613 and 623 formed by second surfaces 614 and 624, coupling portions 617 and 627, restriction portions 618 and 628, and implantation rod securing assemblies comprising set screws 640 and 650. As illustrated in the example embodiment of FIG. 7, system 700 comprises a first body 710, a second body 720, and connecting member 730. First and second bodies 710 and 720 comprise first recessed portions (shown receiving connecting member 730), second recessed portions (only second recessed portion 713 of the first body 710 is shown), coupling portions 717 and 727, restriction portions (only first body restriction portion 718 and connecting member restriction portion 738 is shown), and implantation rod securing assemblies comprising set screws 740 and 750. The connecting member 730 may comprise an elongated portion 731a, a first end 731b, a second end 731c, and connecting member restriction portions 738. The connecting member restriction portions 738 may be received in first body restriction portion 718. In another example embodiment, the first body may comprise a top loading body and the second body may comprise a bottom loading body. In another example embodiment, the first body may comprise a top loading body and the second body may comprise a side loading body. An example embodiment of such configuration is illustrated in FIG. 5. In another example embodiment, the first body may comprise a bottom loading body and the second body may comprise a bottom loading body. In another example embodiment, the first body may comprise a bottom loading body and the second body may comprise a side loading body. In another example embodiment, the first body may comprise a side loading body and the second body may comprise a side loading body. Other combinations are also contemplated in example embodiments, including configurations that are not front loading, top loading, bottom loading, or side loading, such as combination, in-between, shared, and/or diagonal configurations, or the like.

An example implementation for securing an implantation rod connector system with one or more implantation rods will now be described. A first step may comprise a selection of an appropriate configuration for the implantation rod connector system. The selection may be based on, among other things, the particular situation of the patient, the desired or required orientation, position, and/or spacing of the implantation rod(s), the existing orientation, position, and/or spacing of already implanted implantation rod(s), availability of parts, etc.

Once a suitable configuration of the implantation rod connector system has been selected and an installation location of the implantation rod connector system along the one or more implantation rods has been identified, the implantation rod connector system may be secured to the implantation rod(s). For illustration purposes, the selected configuration is the example embodiment of FIGS. 1A, 1B, and 1C. The first body 110 (or alternatively, the second body 120) may be provided to receive a first implantation rod portion in the second recessed portion 113 of the first body 110. The first set screw 140 may then be provided to the first set screw recessed portion 115, such as by threading. The first set screw 140 may be engaged in the substantially locked position at this or at a later stage. The second body 120 may then be provided to receive a second implantation rod portion in the second recessed portion 123 of the second body 120. The second set screw 150 may then be provided to the second set screw recessed portion 125, such as by threading. The second set screw 150 may be engaged in the substantially locked position at this or at a later stage. An example reason for deferring the engaging of the first set screw 140 and/or the second set screw 150 in the substantially locked position until a later stage is to enable flexibility and adaptability in controlling positioning and orientation of the first body 110 and/or second body 120 along the implantation rod(s) and with respect to each other before fixedly securing the first body 110 relative to the second body 120. In situations wherein the connecting member 130 is not already provided in the first recessed portion 111 of the first body 110 and/or the first recessed portion 121 of the second body 120, such may be performed at this stage. When the desired orientation of the first body 110 relative to the second body 120 about the common axis A and the desired position of the first body 110 and the second body 120 relative to the implantation rod(s) are achieved, the overall system 100 may be secured, that is, engaged in the substantially locked position. To achieve this, the first restriction portion 118 may be mated (or interlocked) with the second restriction portion 128, and the connecting member 130 may be subsequently engaged in the substantially locked position so as to persistently urge the mating of the first restriction portion 118 and the second restriction portion 128 together. Either before or after such mating, the first set screw 140 and/or the second set screw 150 may be engaged in the substantially locked position, if such has not already been completed in one or more prior steps. In situations wherein multiple said steps are performable in or about the same time, such as when more than one set of hands are available, the installation of the implantation rod connector system 100, including the engaging of the connecting member 130, the first set screw 140, and/or the second set screw 150 in the substantially locked position, may be performable in or about the same time.

It is recognized herein that, in persistently urging the mating of the first restriction portion 118 and the second restriction portion 128 together and engaging the first set screw 140, the second set screw 150, and the connecting member 130 in their respective substantially locked positions, example embodiments are operable to solve the above-described conventional problems. Example embodiments are operable to achieve this by enabling the securing of a first implantation rod portion with a second implantation rod portion in ideal and non-ideal situations without requiring, among other things, implantation rod adjustments, such as bending, and/or complicated surgical re-adjustments.

As illustrated in FIGS. 2A, 2B, and 2C, an example embodiment of implantation rod connector system 200 may also comprise a first body 210, a second body 220, and a connecting member 230 operable to be received in one or more first recessed portions (not shown) of the first body 210 and the second body 220. In the example embodiment, each of the first body 210 and the second body 220 comprises two first recessed portions in coupling portions 217 and 227 operable to receive the connecting member 230. It is to be understood herein that the first body 210 and the second body 220 may comprise any number of first recessed portions for receiving the connecting member 230.

Connecting member 230 may comprise an elongated portion 231a with a first end portion 231b, the first end portion 231b in communication with and/or operable to be securely received by the elongated portion 231a. The first end portion 231b may comprise one or more restriction portions 238 of the connecting member 230 receivable by one or more corresponding restriction portions 218 and/or 228 of the first body 210 and/or the second body 220, respectively. The restriction portions of the connecting member, the first body, and the second body may be one or more recessed portions and/or protruded portions. In the example embodiment illustrated in FIGS. 2A, 2B, and 2C, the restriction portions 238 for the connecting member 230 comprise a plurality of protruding portions and the restriction portions 218 and 228 of the first body 210 and the second body 220 comprise a plurality of recessed portions operable to receive the plurality of protruded portions of the restriction portion 238 of the connecting member 230.

It is to be understood herein that, in a similar manner as described for the first and the second restriction portions 118 and 128 of the example embodiment illustrated in FIGS. 1A, 1B, and 1C, the restriction portions 218, 228, and 238 of the first body 210, the second body 220, and the connecting member 230, respectively, are also operable to securably restrict movement, including rotational and translational movement, of the first body 210 relative to the second body 220 about the common longitudinal axis A when engaged in the substantially locked position. For example, such can be achieved when the restriction portions 218, 228, and/or 238 of the first body, the second body, and/or the connecting member 230, respectively, are mated and persistently urged together by the connecting member 230. The connecting member 230 may perform such persistent urging when coupled with one or more corresponding coupling portions 231c, such as a coupling element (example, a nut) at the second end 231c of the connecting member 230. It is also to be understood herein that other portions of the connecting member 230 may be operable to perform or assist in performing the functions of the restriction portions. For example, the coupling element 231c and the surface of second recessed portion of the second body 220 may cooperate to restrict movement, including rotational and translational, of the second body 220 relative to the first body 210 about the common longitudinal axis A. Furthermore, it is to be understood herein that the example embodiment of FIGS. 2A, 2B, and 2C is also operable to enable the first body 210 and the second body 220 to rotate with respect to the common longitudinal axis A and/or with respect to each other when not engaged in the substantially locked position.

As can be seen, the first body 210 and the second body 220 comprise a front loading body. The first body 210 comprises a front side 219a, a back side (not shown), a top side 219c, a bottom side (not shown), a left side (not shown), and a right side 219f. The second body 220 comprises a front side (not shown), a back side 229b, a top side 229c, a bottom side (not shown), a left side 229e, and a right side (not shown). The implantation rod securing assembly of the first body 210 comprises a first set screw recessed portion formed by a first set screw recessed surface and a first set screw 240, and the implantation rod securing assembly of the second body 220 comprises a second set screw recessed portion formed by a second set screw recessed surface and a second set screw 250. Each of the first and second set screw recessed portions are operable to receive the first and second set screws 240 and 250. In a similar manner as described herein for the example embodiments illustrated in FIGS. 1A, 1B, and 1C, when a first implantation rod portion (not shown) and a second implantation rod portion (not shown) are received in the second recessed portion 213 of the first body 210 and the second recessed portion (not shown) of the second body 220, respectively, the first and second set screws 240 and 250 are operable to be engaged in a substantially locked position to secure the implantation rod portions with respect to the first body 210 and the second body 220.

Figure 3A:
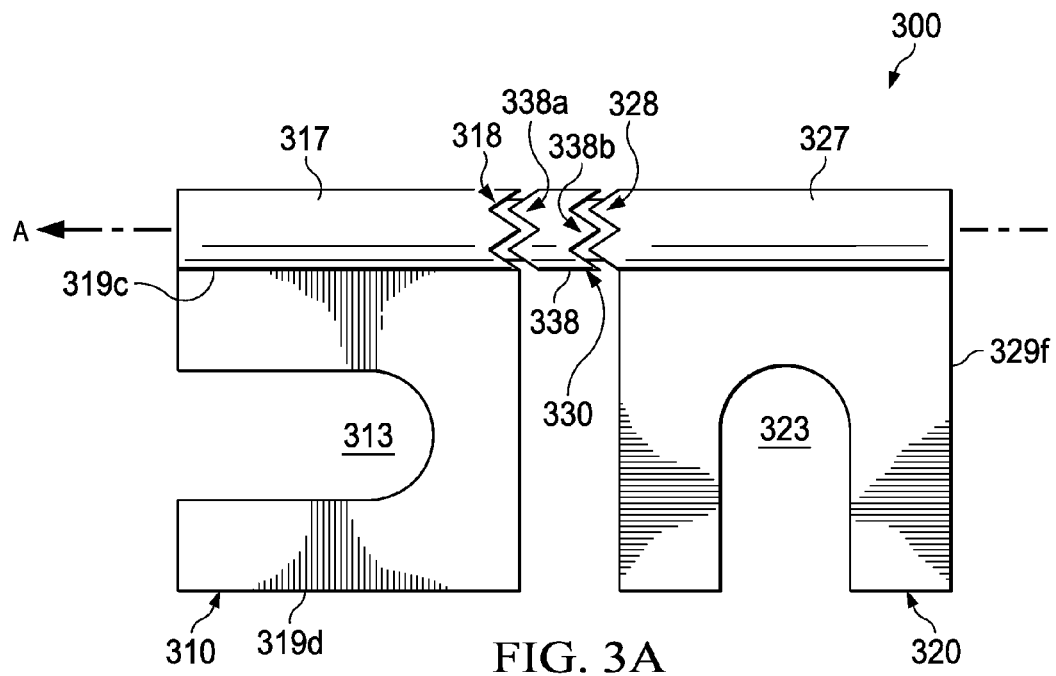
FIG. 3A is an example illustration of a front view of another example embodiment of an implantation rod connector system.
Figure 3B:
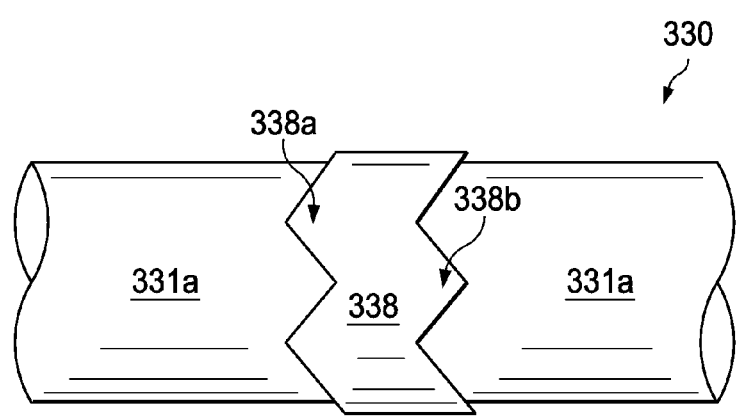
FIG. 3B is an example illustration of a side view of an example embodiment of a connecting member of an implantation rod connector system.

In another example embodiment illustrated in FIGS. 3A and 3B, implantation rod connector system 300 comprises a first body 310, a second body 320, and a connecting member 330. The connecting member 330 may comprise an elongated portion 331a and one or more protruding (or recessed, not shown) restriction portions 338 formed along the elongated portion 331a of the connecting member 330. The one or more restriction portions 338 may comprise portions 338a and/or 338b operable to be securely received by one or more corresponding first and/or second restriction portions 318 and 328 of the first body 310 and/or the second body 320, respectively. As with the example embodiments illustrated in FIGS. 1A-C and 2A-C, the restriction portions 318, 328, 338a, and 338b of the first body 310, the second body 320, and the restriction portion 338 of the connecting member 330, respectively, are also operable to securably restrict movement, including rotational and translational movement, of the first body 310 relative to the second body 320 about the common longitudinal axis A. For example, such can be achieved when the restriction portions 318, 328, 338a, and 338b of the first body 310, the second body 320, and the restriction portion 338 of the connecting member 330, respectively, are mated and persistently urged together by the connecting member 330. The connecting member 330 may perform such persistent urging when coupled with one or more corresponding coupling portions, such as a coupling element (not shown) at one or more of the first and second ends of the connecting member 330, such as a head and/or nut. Furthermore, it is to be understood herein that the example embodiment of FIGS. 3A and 3B is also operable to enable the first body 310 and the second body 320 to rotate with respect to the common longitudinal axis A and/or with respect to each other when not engaged in the substantially locked position.

As can be seen, the first body 310 comprises a left side loading body and the second body 320 comprises a bottom loading body. The implantation rod securing assembly of the first body 310 comprises a first set screw recessed portion formed by a first set screw recessed surface and a first set screw (not shown), and the implantation rod securing assembly of the second body 320 comprises a second set screw recessed portion formed by a second set screw recessed surface and a second set screw (not shown). Each of the first and second set screw recessed portions are operable to receive the first and second set screws. It is to be understood herein that the first and second set screw recessed portions may coincide with a portion of the second recessed portion 313 of the first body 310 and the second recessed portion 323 of the second body 320 in example embodiments. Alternatively or in addition, the first set screw recessed portion may be formed about the top side 319c of the first body 310 and the second set screw recessed portion may be formed about the right side 329f of the second body 320 in example embodiments. Alternatively or in addition, the first and second set screw recessed portions may be formed on any one or more of the top side, the bottom side, the left side, and the right side. In a similar manner as described herein for example embodiments illustrated in FIGS. 1A, 1B, and 1C, when a first implantation rod portion (not shown) and a second implantation rod portion (not shown) are received in the second recessed portion 313 of the first body 310 and the second recessed portion 323 of the second body 320, respectively, the first and second set screws are operable to be engaged in a substantially locked position to secure the implantation rod portions with respect to the first body 310 and the second body 320.

Example embodiments of the implantation rod connector system may be adaptably configurable in other ways. In an example embodiment, the first body may comprise one or more implantation rod securing assemblies and the second body may comprise one or more implantation rod securing assemblies. As previously explained, an implantation rod securing assembly is operable to secure an implantation rod portion to the first and/or second body. As illustrated in FIG. 4, an example embodiment of implantation rod connector system 400 comprises a first body 410 and a second body 420, the first body 410 comprising two implantation rod securing assemblies and the second body 420 comprising one implantation rod securing assembly. It should be noted that FIG. 4 is merely intended to illustrate an example configuration of implantation rod securing assemblies of the first body and the second body, and as such does not illustrate a connecting member and restriction portions, although example embodiments may comprise a connecting member and one or more restriction portions. As can be seen, the first body 410 comprises a front loading body. Each of the two implantation rod securing assemblies of the first body 410 comprise a first set screw recessed portion formed by a first set screw recessed surface and a first set screw 440a and 440b. Each of the two first set screw recessed portions are operable to receive first set screws 440a and 440b. When a first implantation rod portion (not shown) is received in the first recessed portion 413 of the first body 410 and at least one of the two first set screws 440a and 440b are engaged in a substantially locked position, the at least one of the two first set screws 440a and 440b are operable to secure the implantation rod with respect to the first body 410.

As can be seen from FIG. 4, the second body 420 comprises a top loading body, which enables a second implantation rod portion to be received in the second body 420 from the top side. It should be noted that the example embodiment may also allow an implantation rod to be received in the second body 420 from the front side, the rear side, and/or diagonally, if needed. The implantation rod securing assembly of the second body 420 comprises a second set screw recessed portion 425 formed by a second set screw recessed surface 426 and a second set screw (not shown). The second set screw recessed portion 425 is operable to receive the second set screw. When a second implantation rod portion (not shown) is received in the second recessed portion 423 of the second body 420, which in this example embodiment also coincides with a portion of the second set screw recessed portion 425, and the second set screw is engaged in a substantially locked position, the second set screw is operable to secure the implantation rod with respect to the second body 420.

It is to understood herein that the example embodiment of FIG. 4 is also operable to securably restrict movement, including rotational and translational movement, of the first body 410 relative to the second body 420 about the common longitudinal axis A in a similar manner described above and herein. Furthermore, it is to be understood herein that the example embodiment of FIG. 4 is also operable to enable the first body 410 and the second body 420 to rotate with respect to the common longitudinal axis A and/or with respect to each other when not engaged in the substantially locked position.

In another example embodiment illustrated in FIG. 5, the implantation rod connector system 500 comprises a first body 510 and a second body 520, the first body 510 comprising two implantation rod securing assemblies and the second body 520 comprising two implantation rod securing assemblies. As with FIG. 4, it should be noted that FIG. 5 is also merely intended to illustrate an example configuration of implantation rod securing assemblies of the first body and the second body, and as such does not illustrate a connecting member and restriction portions, although example embodiments may comprise a connecting member and one or more restriction portions.

As can be seen from FIG. 5, the first body 510 comprises a top loading body, which enables a first implantation rod portion (not shown) to be received in the first body 510 from the top side. It should be noted that the example embodiment may also allow an implantation rod to be received in the first body 510 from the front side, the rear side, and/or diagonally, if needed. The first body 510 is provided with two first set screw recessed portions 515a and 515b formed by two first set screw recessed surfaces 516a and 516b. Each of the two first set screw recessed portions 515a and 515b are operable to receive first set screws (not shown). When a first implantation rod portion (not shown) is received in the second recessed portion 513 of the first body 510, which also coincides with a portion of the first set screw recessed portions 515a and 515b, and the two first set screws are engaged in a substantially locked position, the two first set screws are operable to secure the first implantation rod portion with respect to the first body 510.

As illustrated, the second body 520 comprises a side loading body, which enables a second implantation rod portion (not shown) to be received in the second body 520 from the right side. It should be noted that the example embodiment may also allow an implantation rod to be received in the second body 520 from the front side, the rear side, and/or diagonally, if needed. The second body 520 is provided with two second set screw recessed portions formed by two second set screw recessed surfaces. The second set screw recessed portions are operable to receive two second set screws 550*a* and 550*b*. When a second implantation rod portion (not shown) is received in the second recessed portion 523 of the second body 520 and the second set screws 550*a* and 550*b* are engaged in a substantially locked position, the second set screws 550*a* and 550*b* are operable to secure the second implantation rod portion with respect to the second body 520.

It is to understood herein that the example embodiment of FIG. 5 is also operable to securably restrict movement, including rotational and translational movement, of the first body 510 relative to the second body 520 about the common longitudinal axis A in a similar manner described above and herein. Furthermore, it is to be understood herein that the example embodiment of FIG. 5 is also operable to enable the first body 510 and the second body 520 to rotate with respect to the common longitudinal axis A and/or with respect to each other when not engaged in the substantially locked position.

The implantation rod connector system may be further adaptably configurable in other ways. For example, the first body may comprise one or more first restriction portions, the second body may comprise one or more second restriction portions, and the connecting member may comprise one or more restriction portions. In an example embodiment, the one or more first restriction portions of the first body may cooperate with one or more second restriction portions of the second body to restrict movement of the first body relative to the second body about the common axis. Example embodiments of such configuration are illustrated in FIGS. 1A, 1B, 1C, and 6. In another example embodiment, the one or more first restriction portions of the first body may cooperate with one or more restriction portions of the connecting member, and one or more second restriction portions of the second body as well, to restrict movement of the first body relative to the second body about the common axis. Example embodiments of such configuration are illustrated in FIGS. 2A, 2B, 3A, and 7.

Example embodiments may further comprise an extension member (not shown) having one or more extension member recessed portions. When installed, the extension member may be positionable on either side of the first body and/or the second body, such as in between the first body and the second body. The extension member may further comprise one or more extension member restriction portions operable to mate with a corresponding restriction portion of the first body, the second body, and/or the connecting member. In this regard, the implantation rod connector system is operable to be adjustably adaptable to different spacing requirements between the first implantation rod portion and the second implantation rod portion, while still securably restricting movement, including rotational and translational movement, of the first body relative to the second body about the common longitudinal axis A in a similar manner described above and herein.

It is to be understood herein that, although example embodiments described above may directable to securing a first implantation rod portion of a first implantation rod with a second implantation rod portion of a second implantation rod, wherein the first implantation rod is different from the second implantation rod, example embodiments described herein may also be applicable to securing two different portions of a single implantation rod and securing more than two implantation rods. For example, a single implantation rod having already been adjusted (or bent, such as in a U-shape) may be securable using example embodiments described herein. For such implantation rods, a first implantation rod portion of the implantation rod may be securably received by a first body and a second implantation rod portion of the same implantation rod may be securably received by a second body. As another example, two implantation rods may be securably received by a first body or a second body. As another example, a third body separate from the first body and the second body may also be in communication with the connecting member. In such an example embodiment, the third body may be operable to securely receive a first implantation rod, a second implantation rod, and/or a third implantation rod.

While various example embodiments in accordance with the disclosed principles have been described above, it should be understood herein that the example embodiments have been presented by way of example only, and are not limiting. Thus, the breadth and scope of the example embodiments should not be limited by any of the above-described example embodiments, but should be defined only in accordance with the claims and their equivalents issuing from this disclosure. Furthermore, the above advantages and features are provided in example embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. An apparatus for use in securing one or more surgically implantable implantation rods, the apparatus comprising:
a first body having a first recessed portion of the first body formed by a first surface of the first body;
a second body having a first recessed portion of the second body formed by a first surface of the second body;
a connecting member having an elongated body defining a common longitudinal axis for the first body and the second body, the connecting member receivable in the first recessed portion of the first body and the first recessed portion of the second body; and
a third body having a first recessed portion of the third body operable to receive the connecting member;
wherein the connecting member is operable to cooperate with the first body to restrict movement of the first body relative to the second body about the common longitudinal axis when engaged in a substantially locked position, and the first body is moveable relative to the second body when disengaged from the substantially locked position;

wherein the third body further comprises a second recessed portion of the third body operable to receive a third implantation rod portion; and wherein the third body further comprises a third restriction portion operable to cooperate with one or more of a first restriction portion of the first body, a second restriction portion of the second body, and a protruding portion of the connecting member to restrict movement of the first body, the second body, and the third body relative to each other about the common longitudinal axis.

2. The apparatus of claim 1, wherein the first body further comprises a second recessed portion of the first body formed by a second surface of the first body, wherein the second body further comprises a second recessed portion of the second body formed by a second surface of the second body, and wherein the second recessed portion of the first body and the second recessed portion of the second body are operable to receive a first implantation rod portion and a second implantation rod portion, respectively.

3. The apparatus of claim 2, wherein the first body and the second body further comprise a first implantation rod securing assembly and a second implantation rod securing assembly, respectively, operable to secure the first implantation rod portion and the second implantation rod portion, respectively, in the second recessed portion of the first body and the second body, respectively, when the first implantation rod securing assembly and the second implantation rod securing assembly are engaged in a substantially locked position, respectively.

4. The apparatus of claim 3, wherein the first implantation rod securing assembly comprises a first set screw and a first set screw recessed portion operable to receive the first set screw.

5. The apparatus of claim 3, wherein the second implantation rod securing assembly comprises a second set screw and a second set screw recessed portion operable to receive the second set screw.

6. The apparatus of claim 1, wherein the first body further comprises a first restriction portion being one or more of a recessed portion and a protruding portion of the first restriction portion formed by a surface of the first restriction portion, the first restriction portion operable to restrict movement of the first body relative to the second body about the common longitudinal axis when the first restriction portion is engaged in a substantially locked position.

7. The apparatus of claim 1, wherein the second body further comprises a second restriction portion being one or more of a recessed portion and a protruded portion of the second restriction portion formed by a surface of the second restriction portion, the second restriction portion operable to restrict movement of the first body relative to the second body about the common longitudinal axis when the second restriction portion is engaged in a substantially locked position.

8. The apparatus of claim 1, wherein the first body further comprises a first restriction portion being one or more of a recessed portion and a protruding portion of the first restriction portion formed by a surface of the first restriction portion, the first restriction portion operable to restrict movement of the first body relative to the second body about the common longitudinal axis when the first restriction portion is engaged in a substantially locked position, and wherein the second body further comprises a second restriction portion being one or more of a recessed portion and a protruded portion of the second restriction portion formed by a surface of the second restriction portion, the second restriction portion operable to restrict movement of the first body relative to the second body about the common longitudinal axis when the second restriction portion is engaged in a substantially locked position.

9. The apparatus of claim 8, wherein the first and second restriction portions are engaged in the substantially locked position when the first restriction portion and the second restriction portion are engaged in an interlocking manner.

10. The apparatus of claim 6, wherein the connecting member further comprises a connecting member protruded portion, the connecting member protruded portion operable to engage in an interlocking manner with the first restriction portion.

11. The apparatus of claim 7, wherein the connecting member further comprises a connecting member protruded portion, the connecting member protruded portion operable to engage in an interlocking manner with the second restriction portion.

12. The apparatus of claim 1, wherein the connecting member is further operable to restrict translational movement of the first body relative to the second body when the connecting member is engaged in a substantially locked position.

13. The apparatus of claim 3, wherein the first body further comprises a top side, a bottom side, a front side, a back side, a left side, and a right side, and wherein the second recessed portion of the first body is further definable by one or more openings about at least one of the top side, the bottom side, the front side, the back side, the left side, and the right side of the first body, the one or more openings operable to receive insertion of the first implantation rod portion before the first implantation rod securing assembly is engaged in the substantially locked position.

14. The apparatus of claim 3, wherein the second body further comprises a top side, a bottom side, a front side, a back side, a left side, and a right side, and wherein the second recessed portion of the second body is further definable by one or more openings about at least one of the top side, the bottom side, the front side, the back side, the left side, and the right side of the second body, the one or more openings operable to receive insertion of the second implantation rod portion before the second implantation rod securing assembly is engaged in the substantially locked position.

15. The apparatus of claim 1, wherein one or more of the first body and the second body comprises a front loading body, wherein the front loading body comprises one or more openings about at least one or more of a front side and a back side, the one or more openings operable to receive insertion of a portion of an implantation rod.

16. The apparatus of claim 1, wherein one or more of the first body and the second body comprises a top loading body, wherein the top loading body comprises one or more openings about at least a top side, the one or more openings operable to receive insertion of a portion of an implantation rod.

17. The apparatus of claim 1, wherein one or more of the first body and the second body comprises a bottom loading body, wherein the bottom loading body comprises one or more openings about at least a bottom side, the opening operable to receive insertion of a portion of an implantation rod.

18. The apparatus of claim 1, wherein one or more of the first body and the second body comprises a left side loading body, wherein the left side loading body comprises one or more openings about at least a left side, the one or more openings operable to receive insertion of a portion of an implantation rod.

19. The apparatus of claim 1, wherein one or more of the first body and the second body comprises a right side loading body, wherein the right side loading body comprises one or more openings about at least a right side, the one or more openings operable to receive insertion of a portion of an implantation rod.

20. The apparatus of claim 1, wherein the first body comprises one of a front loading body, a top loading body, a bottom loading body, a left side loading body, and a right side loading body, and wherein the second body comprises substantially the same body as the first body.

21. The apparatus of claim 1, wherein the first body comprises one of a front loading body, a top loading body, a bottom loading body, a left side loading body, and a right side loading body, and wherein the second body comprises a different type of loading body to the first body.

22. The apparatus of claim 3, wherein the first body further comprises a third implantation rod securing assembly operable to further secure the first implantation rod portion in the second recessed portion of the first body when the third implantation rod securing assembly is engaged in a substantially locked position.

23. The apparatus of claim 3, wherein the second body further comprises a fourth implantation rod securing assembly operable to further secure the second implantation rod portion in the second recessed portion of the second body when the fourth implantation rod securing assembly is engaged in a substantially locked position.

24. The apparatus of claim 1, further comprising an extension portion having a first recessed portion of the extension portion, the first recessed portion of the extension portion operable to receive the connecting member and cooperate with one or more of the first body and the second body to restrict movement of the first body relative to the second body about the common longitudinal axis.

25. An apparatus for use in securing one or more surgically implantable implantation rods, the apparatus comprising:
- a connecting member comprising an elongated body defining a common longitudinal axis;
- a first body comprising a first recessed portion of the first body operable to receive the connecting member and a second recessed portion of the first body operable to receive a first implantation rod portion, the first and second recessed portions of the first body formed by a first and a second surface of the first body, respectively, the first body further comprising a first set screw and a first set screw recessed portion operable to receive the first set screw and defining a first set screw axis;
- a second body comprising a first recessed portion of the second body operable to receive the connecting member and a second recessed portion of the second body operable to receive a second implantation rod portion, the first and second recessed portions of the second body formed by a first and a second surface of the second body, respectively, the second body further comprising a second set screw and a second set screw recessed portion operable to receive the second set screw and defining a second set screw axis;
- a first restriction portion comprising one or more of a recessed portion and a protruding portion of the first restriction portion formed by a surface of the first restriction portion; and
- a second restriction portion comprising one or more of a recessed portion and a protruding portion of the second restriction portion formed by a surface of the second restriction portion;
- wherein movement of the first body relative to the second body about the common longitudinal axis is restrictable when the first restriction portion and the second restriction portion are engaged in an interlocking manner and the connecting member is secured in the first body and the second body; and
- wherein at least one of the first set screw axis and the second set screw axis is perpendicular to the common longitudinal axis.

26. The apparatus of claim 25, wherein the first body and the second body further comprise a first implantation rod securing assembly and a second implantation rod securing assembly, respectively, the first and second implantation rod securing assemblies operable to secure the first implantation rod portion and the second implantation rod portion, respectively, in the first recessed portion of the first body and the second body, respectively, when each of the first and second implantation rod securing assemblies are engaged in a substantially locked position, respectively.

27. The apparatus of claim 25, wherein the first restriction portion forms a part of the first body and the second restriction portion forms a part of the second body.

28. The apparatus of claim 25, further comprising a third restriction portion comprising one or more of a recessed portion and a protruding portion of the third restriction portion formed by a surface of the third restriction portion.

29. The apparatus of claim 28, wherein the first restriction portion forms a part of the first body, the second restriction portion forms a part of the second body, and the third restriction portion forms a part of the connecting member, and wherein the first, the second, and the third restriction portions are interlocked in a secured manner when the connecting member is secured in the first body and the second body.

30. The apparatus of claim 25, wherein the first restriction portion forms a part of the first body and the second restriction portion forms a part of the connecting member.

31. An apparatus for use in securing one or more surgically implantable implantation rods, the apparatus comprising:
- a connecting member comprising a first end formed by a first end outer surface, a second end formed by a second end outer surface, and an elongated body in communication with the first end and the second end, the elongated body operable to define a common longitudinal axis;
- a first body comprising:
  - a first recessed portion of the first body operable to receive at least the first end of the connecting member, the first recessed portion of the first body formed by a first surface of the first body;
  - a second recessed portion of the first body operable to receive a first implantation rod portion, the second recessed portion of the first body formed by a second surface of the first body; and
  - a first restriction portion comprising one or more of a recessed portion and a protruding portion of the first restriction portion formed by a third surface of the first body;
- a second body comprising:
  - a first recessed portion of the second body operable to receive at least the second end of the connecting member, the first recessed portion of the second body formed by a first surface of the second body;
  - a second recessed portion of the second body operable to receive a second implantation rod portion, the second recessed portions of the second body formed by a second surface of the second body; and
  - a second restriction portion comprising one or more of a recessed portion and a protruding portion of the second restriction portion formed by a third surface of the second body;

wherein movement of the first body relative to the second body about the common longitudinal axis is restrictable when the one or more of the recessed portion and the protruding portion of the first restriction portion and the one or more of the recessed portion and the protruding portion of the second restriction portion are mated and persistently urged together by the connecting member.

32. The apparatus of claim 31, wherein the first body and the second body further comprise a first implantation rod securing assembly and a second implantation rod securing assembly, respectively, the first and second implantation rod securing assemblies operable to secure the first implantation rod portion and the second implantation rod portion, respectively, in the first recessed portion of the first body and the second body, respectively, when each of the first and second implantation rod securing assemblies are engaged in a substantially locked position, respectively.

33. The apparatus of claim 31, further comprising a third restriction portion comprising one or more of a recessed portion and a protruding portion of the third restriction portion formed by a surface of the third restriction portion.

34. The apparatus of claim 33, wherein the third restriction portion forms a part of the connecting member, and wherein one or more of the first and the second restriction portions are mated and persistently urged together with the third restriction portion by the connecting member.

* * * * *